(12) United States Patent
Eidenschink

(10) Patent No.: US 8,398,698 B2
(45) Date of Patent: Mar. 19, 2013

(54) BIFURCATED STENT DELIVERY SYSTEM

(75) Inventor: Tracee E. J. Eidenschink, Wayzata, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 578 days.

(21) Appl. No.: 12/352,007

(22) Filed: Jan. 12, 2009

(65) Prior Publication Data

US 2009/0182406 A1 Jul. 16, 2009

Related U.S. Application Data

(60) Continuation of application No. 10/626,794, filed on Jul. 22, 2003, now Pat. No. 7,476,243, which is a division of application No. 09/490,808, filed on Jan. 26, 2000, now abandoned.

(60) Provisional application No. 60/117,351, filed on Jan. 27, 1999.

(51) Int. Cl.
*A61F 2/06* (2006.01)
(52) U.S. Cl. ..................................... 623/1.11
(58) Field of Classification Search ............. 23/1.11; 623/1.11; 604/101.03, 101.01, 102.01, 102.02, 604/102.03
See application file for complete search history.

(56) References Cited

U.S. PATENT DOCUMENTS

| | | | |
|---|---|---|---|
| 3,884,242 A | 5/1975 | Bazell et al. | |
| 4,696,668 A * | 9/1987 | Wilcox | 604/28 |
| 4,774,949 A | 10/1988 | Fogarty | |
| 4,921,483 A * | 5/1990 | Wijay et al. | 604/103.1 |
| 4,950,227 A | 8/1990 | Savin et al. | |
| 4,958,634 A * | 9/1990 | Jang | 606/194 |
| 4,994,071 A | 2/1991 | MacGregor | |
| 4,998,923 A | 3/1991 | Samson et al. | |
| 5,002,532 A * | 3/1991 | Gaiser et al. | 604/101.01 |
| 5,147,377 A * | 9/1992 | Sahota | 606/194 |
| 5,163,906 A * | 11/1992 | Ahmadi | 604/101.03 |
| 5,304,132 A * | 4/1994 | Jang | 604/101.01 |
| 5,320,605 A | 6/1994 | Sahota | |
| 5,413,581 A | 5/1995 | Goy | |
| 5,569,201 A | 10/1996 | Burns | |
| 5,607,444 A | 3/1997 | Lam | |
| 5,609,605 A | 3/1997 | Marshall et al. | |
| 5,613,980 A | 3/1997 | Chauhan | |
| 5,669,924 A | 9/1997 | Shaknovich | |
| 5,697,971 A | 12/1997 | Fischell et al. | |
| 5,720,735 A | 2/1998 | Dorros | |
| 5,749,825 A | 5/1998 | Fischell et al. | |
| 5,755,735 A | 5/1998 | Richter et al. | |
| 5,775,734 A | 7/1998 | George, Jr. | |
| 5,776,101 A | 7/1998 | Goy | |
| 5,810,871 A * | 9/1998 | Tuckey et al. | 606/198 |
| 5,827,320 A | 10/1998 | Richter et al. | |
| 5,961,490 A | 10/1999 | Adams | |
| 6,013,054 A | 1/2000 | Jiun Yan | |

(Continued)

FOREIGN PATENT DOCUMENTS

CA 2227446 12/1997
CA 2237829 11/2006

(Continued)

*Primary Examiner* — Gregory Anderson
(74) *Attorney, Agent, or Firm* — Seager, Tufte & Wickhem LLC

(57) ABSTRACT

The present invention is drawn to a system and/or device for deploying a stent at a bifurcation. In one embodiment, the system and/or device for deploying a stent at a bifurcation may include a dual balloon catheter may include an elongate catheter body. Some dual balloon catheters may have a first proximal balloon and a second balloon bonded to at least a portion of the elongate catheter body. In some cases, a guide wire port may be positioned between the first and second balloons.

17 Claims, 8 Drawing Sheets

U.S. PATENT DOCUMENTS

| | | | |
|---|---|---|---|
| 6,096,073 | A | 8/2000 | Webster et al. |
| 6,117,117 | A * | 9/2000 | Mauch .................... 604/284 |
| 6,143,002 | A | 11/2000 | Vietmeier |
| 6,165,195 | A | 12/2000 | Wilson et al. |
| 6,183,509 | B1 | 2/2001 | Dibie |
| 6,210,431 | B1 | 4/2001 | Power |
| 6,221,090 | B1 | 4/2001 | Wilson |
| 6,221,098 | B1 | 4/2001 | Wilson et al. |
| 6,258,534 | B1 | 7/2001 | Laugharn, Jr. et al. |
| 6,287,277 | B1 | 9/2001 | Yan |
| 6,319,275 | B1 | 11/2001 | Lashinski et al. |
| 6,325,826 | B1 | 12/2001 | Vardi et al. |
| 6,346,089 | B1 | 2/2002 | Dibie |
| 6,361,544 | B1 | 3/2002 | Wilson et al. |
| 6,361,558 | B1 | 3/2002 | Hieshima et al. |
| 6,371,978 | B1 | 4/2002 | Wilson |
| 6,379,372 | B1 | 4/2002 | Dehdashtian et al. |
| 6,428,567 | B2 | 8/2002 | Wilson et al. |
| 6,436,104 | B2 | 8/2002 | Hojeibane |
| 6,440,161 | B1 | 8/2002 | Madrid et al. |
| 6,475,166 | B1 | 11/2002 | Escano |
| 6,482,211 | B1 | 11/2002 | Choi |
| 6,488,694 | B1 | 12/2002 | Lau et al. |
| 6,508,836 | B2 | 1/2003 | Wilson et al. |
| 6,514,281 | B1 | 2/2003 | Blaeser et al. |
| 6,582,394 | B1 | 6/2003 | Reiss et al. |
| 7,476,243 | B2 | 1/2009 | Eidenschink |

FOREIGN PATENT DOCUMENTS

| | | |
|---|---|---|
| EP | 0515201 | 9/1997 |
| EP | 0897700 | 2/1999 |
| EP | 0698380 | 2/2002 |
| EP | 0646365 | 1/2004 |
| WO | 9214508 | 9/1992 |
| WO | 9304722 | 3/1993 |
| WO | 9634580 | 5/1996 |
| WO | 9716217 | 5/1997 |
| WO | 9746174 | 12/1997 |
| WO | 9836709 | 8/1998 |
| WO | 9824104 | 5/1999 |
| WO | 9944539 | 9/1999 |

* cited by examiner

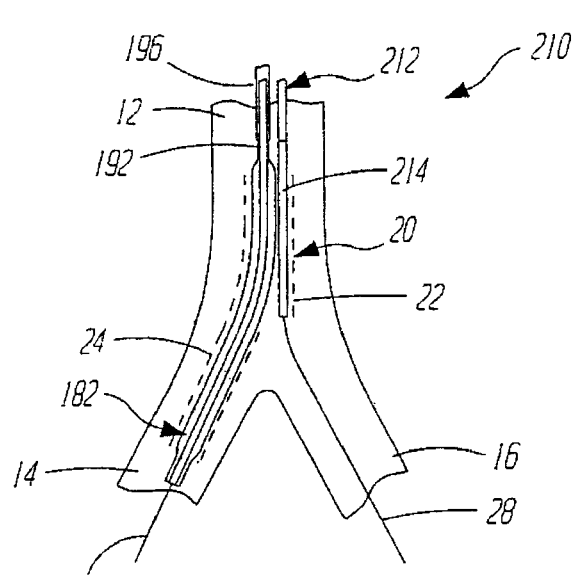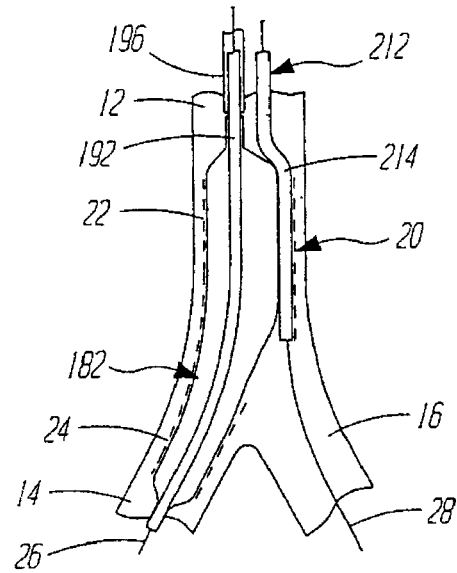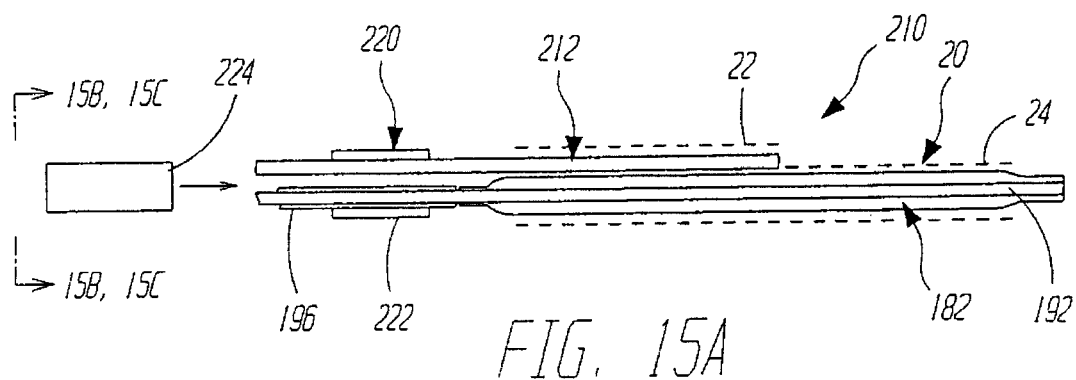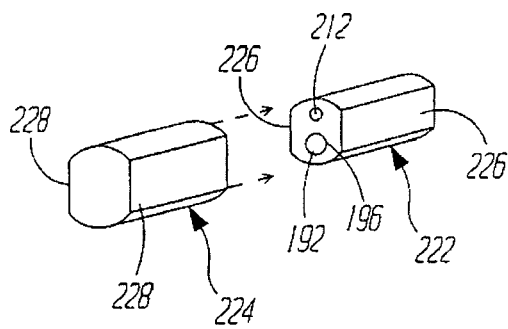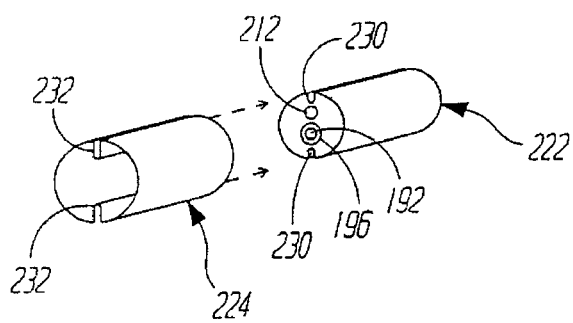

BIFURCATED STENT DELIVERY SYSTEM

RELATED APPLICATIONS

This application is a continuation of U.S. application Ser. No. 10/626,794, now U.S. Pat. No. 7,476,243, filed Jul. 22, 2003, titled "BIFURCATION STENT DELIVERY SYSTEM", which is a divisional of U.S. application Ser. No. 09/490,808, filed Jan. 26, 2000, now abandoned, which claims priority to U.S. Provisional Application No. 60/117,351, filed Jan. 27, 1999, all of which are hereby incorporated by reference in their entirety.

U.S. Pat. No. 4,950,227 issued Aug. 21, 1990 to Savin et al. entitled "STENT DELIVERY SYSTEM" and assigned to Boston Scientific Corporation is hereby incorporated by reference.

Reference is hereby made to the following U.S. issued patents:

U.S. Pat. No. 6,258,534 (Ser. No. 09/035,652) filed Mar. 5, 1998, entitled "DILATATION AND STENT DELIVERY SYSTEM FOR BIFURCATION LESIONS";

U.S. Pat. No. 6,096,073 (Ser. No. 09/028,792) filed Feb. 24, 1998, entitled "STENTS AND STENT DELIVERY AND DILATATION SYSTEM FOR BIFURCATION LESIONS";

U.S. Pat. No. 6,143,002 (Ser. No. 09/129,472) filed Aug. 4, 1998, entitled "SYSTEM FOR DELIVERING STENTS TO BIFURCATION LESIONS"; and U.S. Pat. No. 6,514,281 (Ser. No. 09/148,179) filed Sep. 4, 1998, entitled "SYSTEM FOR DELIVERING BIFURCATION STENTS".

BACKGROUND

The present invention relates to a system for treating vascular disease. More specifically, the present invention relates to a system for deploying a stent in a bifurcation lesion.

Vascular disease currently represents a prevalent medical condition. Typical vascular disease involves the development of a stenosis in the vasculature. The particular vessel containing the stenosis can be completely blocked (or occluded) or it can simply be narrowed (or restricted). In either case, restriction of the vessel caused by the stenotic lesion results in many well known problems caused by the reduction or cessation of blood circulation through the restricted vessel.

A bifurcation is an area of the vasculature where a first (or parent) vessel is bifurcated into two or more branch vessels. It is not uncommon for stenotic lesions to form in such bifurcations. The stenotic lesions can affect only one of the vessels (i.e., either of the branch vessels or the parent vessel) two of the vessels, or all three vessels.

Vascular stents are also currently well known. Vascular stents typically involve a tubular stent which is movable from a collapsed, low profile, delivery position to an expanded, deployed position. The stent is typically delivered using a stent delivery device, such as a stent delivery catheter. In one common technique, the stent is crimped down to its delivery position over an expandable element, such as a stent deployment balloon. The stent is then advanced using the catheter attached to the stent deployment balloon to the lesion site under any suitable, commonly known visualization technique. The balloon is then expanded to drive the stent from its delivery position to its deployed position in which the outer periphery of the stent frictionally engages the inner periphery of the lumen. In some instances, the lumen is predilated using a conventional dilatation catheter, and then the stent is deployed to maintain the vessel in an unoccluded, and unrestricted position.

Self-expanding stents can also be used. Self-expanding stents are typically formed of a resilient material. The resilient material has sufficient resilience that it can be collapsed to the low profile position and inserted within a delivery device, such as a catheter. Once the catheter is placed at the site of the stenotic lesion, the stent is pushed from within the catheter such that it is no longer constrained in its low profile position. The stent, driven by the resilience of the material, expands to a higher profile, deployed position in which its outer periphery frictionally engages the walls of the stenosed vessel, thereby reducing the restriction in the vessel.

While there have recently been considerable advances in stent design and stent deployment techniques, current methods of treating bifurcation lesions are suboptimal, particularly where both downstream branch vessels are affected by the lesion Current techniques of dealing with such lesions typically require the deployment of a slotted tube stent across the bifurcation. However, this compromises the ostium of the unstented branch.

Further, once the first stent is deployed, the treating physician must then advance a dilatation balloon between the struts of the stent already deployed in order to dilate the second branch vessel. The physician may then attempt to maneuver a second stent through the struts of the stent already deployed, into the second branch vessel for deployment. This presents significant difficulties. For example, dilating between the struts of the stent already deployed tends to distort that stent. Further, deploying the second stent through the struts of the first stent is not only difficult, but it can also distort the first stent. Thus, the current systems used to alternately deploy stents in a bifurcated lesion have significant disadvantages.

Also, since two guidewires are often used to deploy stents at a bifurcation, the guidewires can become crossed, or somewhat entangled. The deployment systems which are advanced along such guidewires can become caught on the wires, where they cross over one another. This can require additional time and manipulation of the stent deployment system in order to properly deploy the stent at the bifurcation.

Further, some branch vessels can have somewhat smaller diameter lumens than the parent vessels from which they branch. Therefore, stents of different sizes need to be deployed in the parent vessel and the branch vessel. Alternatively, a single stent having a larger diameter portion, and one or more smaller diameter portions, can be deployed at the bifurcation. However, this can lead to difficulty in deployment. For instance, a balloon which is sized to fit within the smaller diameter stent portion, and deploy that portion, may not be large enough to deploy the larger diameter stent portion. Therefore, a plurality of balloon catheters must be used to deploy such stents.

SUMMARY

The present invention is drawn to a system and/or device for deploying a stent at a bifurcation. In one embodiment, a dual balloon catheter may include an elongate catheter body that may having a distal end, at least one guide wire lumen therethrough and an inflation lumen therein. The dual balloon catheter may also include a first proximal balloon that may have a proximal portion bonded to the catheter and a second distal balloon that may have a distal portion bonded to the catheter distally of the first balloon, the proximal and distal balloons in fluid communication with the inflation lumen. A guide wire port may be positioned between the first and second balloons and in communication with the at least one guide wire lumen.

The preceding summary is provided to facilitate a general understanding of some of the innovative features unique to the present disclosure and is not intended to be a full description. A full appreciation of the disclosure can be gained by taking the entire specification, claims, drawings, and abstract as a whole.

BRIEF DESCRIPTION OF THE DRAWINGS

FIGS. 14A-14C illustrate a collapsible embodiment of a stepped balloon stent deployment system; and FIGS. 15A-15C illustrate stiffening and torquing systems for use with a stent deployment system.

DETAILED DESCRIPTION

Figure 1:
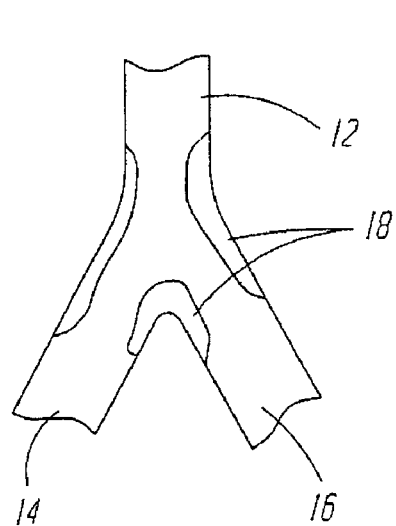
FIG. 1 illustrates a typical bifurcation lesion.

FIG. 1 illustrates bifurcation 10 which includes parent vessel 12, first branch vessel 14 and second branch vessel 16. FIG. 1 also illustrates that a bifurcation lesion 18 has developed in bifurcation 10. As illustrated, lesion 18 extends into both branch vessels 14 and 16, and extends slightly into parent vessel 12 as well. Lesion 18 may also be located on only one side of the branch vessel 14 or 16. In either case, it is preferable to stent both branch vessels 14 and 16 to avoid collapsing one. In order to treat bifurcation lesion 18, it may commonly first be predilated with a conventional angioplasty balloon catheter dilatation device.

Figure 2:
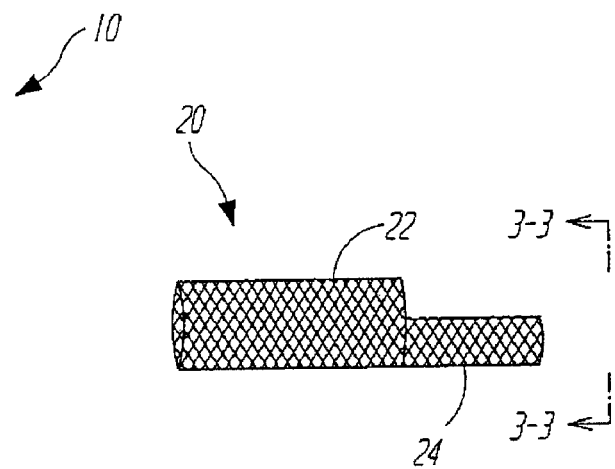
FIGS. 2 and 3 illustrate a stent having two different deployed diameters.

FIG. 2 is a side view of a stent 20 which can be used to treat a portion of bifurcation 10. Stent 20 includes a first portion 22 and a second portion 24. First portion 22 has a relatively large deployed diameter, while second portion 24 has a somewhat smaller deployed diameter.

Figure 3:
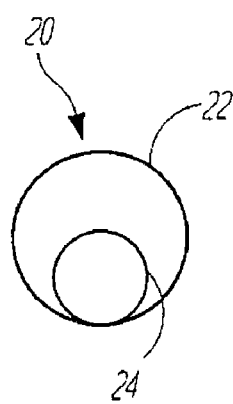

FIG. 3 is an end view of stent 20 taken as indicated by arrows 3-3 in FIG. 2. In one illustrative embodiment, portions 22 and 24 of stent 20 are simply discrete stents which have been interwoven, or attached, to one another. Alternatively, stent 20 can be formed by one integral stent formed with portions 22 and 24 being integral with one another. In either case, stent 20 can preferably be deformed to a low profile, collapsed (or deployment) position in which it can be inserted through parent vessel 12 to bifurcation 10. Stent 20 is then deployed, either using its own resilience, or using a balloon deployment system, to its expanded, deployed position illustrated in FIG. 2.

Figure 4:
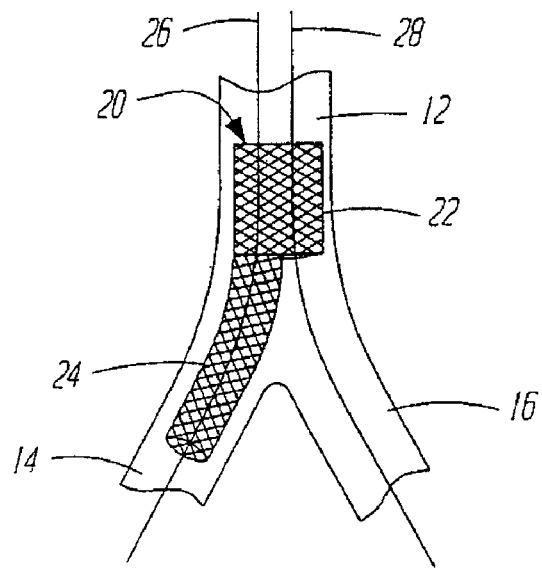
FIG. 4 illustrates the stent shown in FIGS. 2 and 3 deployed in a bifurcation.

FIG. 4 illustrates stent 20 deployed in bifurcation 10. In FIG. 4, first and second guidewires 26 and 28 are first inserted, through parent vessel 12, to bifurcation 10 such that guidewire 26 has a distal end residing in branch vessel 14 while guidewire 28 has a distal end residing in branch vessel 16. Using a stent deployment system, such as any of those described in greater detail later in the specification, stent 20 is advanced in a low profile, insertion position to the location illustrated in FIG. 4. Stent 20 is then deployed by expanding portions 22 and 24 to the deployed positions illustrated in FIG. 4. In one illustrative embodiment, portion 24 has an outer diameter which, when deployed, frictionally engages the inner diameter of branch vessel 14. Similarly, portion 22 has an outer diameter which, when deployed, is sufficient to frictionally engage the inner diameter of parent vessel 12, to remain in place in bifurcation 10.

Figure 5:
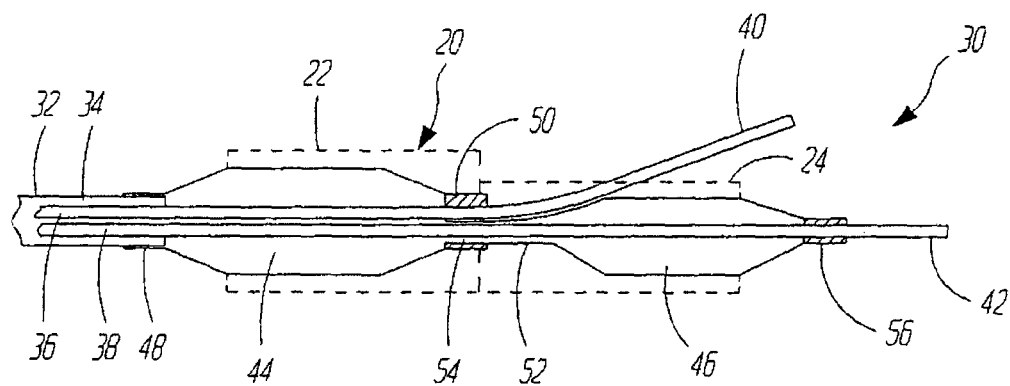
FIG. 5 illustrates a dual-balloon stent deployment system.

FIG. 5 is a side view of a dual-balloon stent deployment system 30 in accordance with one aspect of the present invention. System 30 is shown with a cross-section of stent 20, in the deployed position, disposed thereon. System 30 includes a proximal catheter 32 having a lumen 34 disposed therein. First and second guidewire lumens (or tubes) 36 and 38 extend from within lumen 34 and extend to distal ends 40 and 42. System 30 also includes a first, proximal balloon 44 and a second, distal balloon 46. Balloon 44 has a proximal end 48 which is sealed to the distal end of catheter 32. While proximal end 48 of balloon 44 can be sealed to either the outer or inner side of catheter 32, it is illustrated in FIG. 5 as being sealed to the outer surface of catheter 32, using, for example, an adhesive. Balloon 44 also has a distal end 50 which is sealed, with a fluid tight seal, about guidewire tube 36 and a portion of the proximal end 52 of balloon 46.

Balloon 46 includes a proximal end 52 which is also fluidly sealed partially to an inside surface of the distal waist of balloon 44 and partially to guidewire lumen 38. However, an inflation lumen 54 extends from the interior of balloon 44, through the proximal end 52 of balloon 46, and communicates with the interior or balloon 46. Balloon 46 further includes a distal end 56 which is sealed to the outer surface of guidewire lumen 42. Therefore, an inflation lumen for inflating balloons 44 and 46 is defined by lumen 34 of catheter 42, and lumen 54 disposed about at least a portion of guidewire tubes 36 and 38.

Guidewire lumen 38 extends from lumen 34 distally through both balloons 44 and 46, and protrudes out the distal end 56 of balloon 46. Guidewire lumen 36, on the other hand (and as will be disclosed in greater detail later in the specification) is used to track a guidewire which extends down a branching vessel. Guidewire lumen 38 has a distal end 40 which extends out from within the distal end 50 of balloon 44, and extends to a position outside of balloon 46. Both balloons 44 and 46 can preferably be collapsed to a low profile, insertion position. However, balloon 44 has a relatively large inflated diameter for driving deployment of the larger diameter portion 22 of stent 20. Balloon 46, on the other hand, has a smaller inflated diameter for driving deployment of the smaller diameter stent portion 24 of stent 20.

Figure 6A:
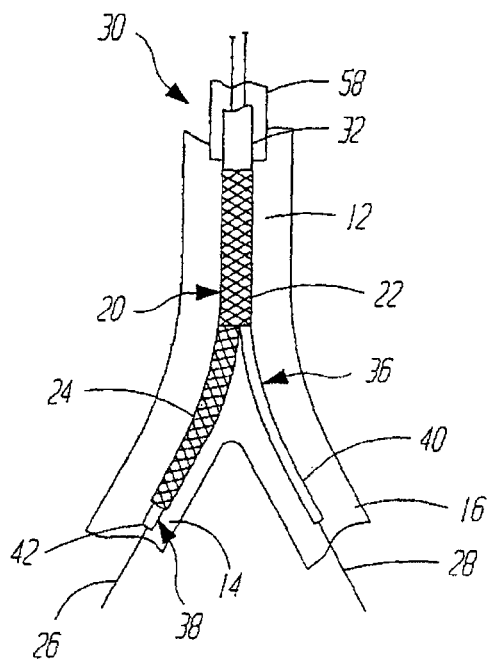
FIGS. 6A and 6B illustrate deployment of the stent deployment system illustrated in FIG. 5.
Figure 6B:
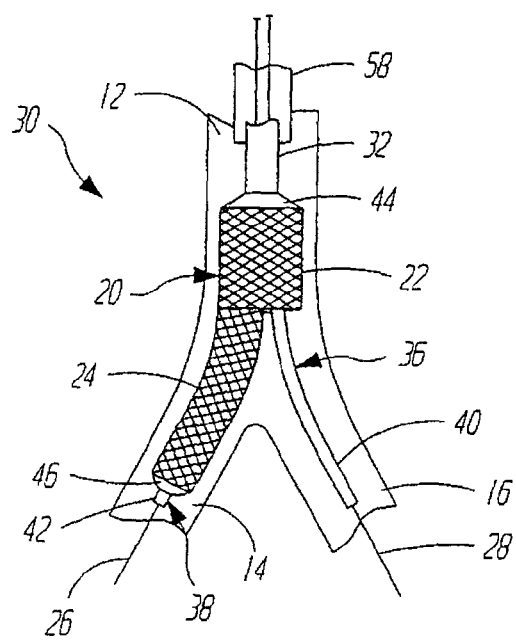

FIGS. 6A and 6B illustrate the deployment of stent 20 utilizing system 30 illustrated in FIG. 5. FIG. 6A illustrates system 30 in the insertion position. First, guidewires 26 and 28 are advanced through the vasculature to bifurcation 10, such that they reside within branch vessels 14 and 16, respectively. It should be noted that system 30 can be backloaded onto guidewires 26 and 28. In that case, prior to inserting guidewires 26 and 28, system 30 is loaded onto the guidewire such that guidewire 26 resides within guidewire tube 36 while guidewire 28 resides within tube 30. Alternatively, system 30 can be loaded onto guidewires 26 and 28 from the proximal end of the guidewires. In either case, after the guidewires are positioned appropriately, system 30 is advanced using catheter 32 through the vasculature (and may be advanced through a guide catheter 58) to bifurcation 10. System 30 is then further advanced such that stent portion 24 follows guidewire 26 and resides within branch vessel 14.

Once in the position illustrated in FIG. 6A, fluid is introduced into balloons 44 and 46 through catheter 32, to inflate the balloons. This drives stent portions 22 and 24 of stent 20 into the deployed position illustrated in FIG. 6B. In the deployed position, the outer diameter of stent portions 22 and 24 are sufficient to frictionally engage the interior vessel walls of parent vessel 12 and branch vessel 14, respectively, such that stent 20 is frictionally held in place in bifurcation 10. The lumens 44 and 46 are then deflated, and system 30 is removed from within stent 20. Guidewires 26 and 28 are then removed from bifurcation 10, leaving stent 20 deployed in place.

System 30 preferably employs balloons 44 and 46 which have steep proximal and distal cone angles in order to reduce any gap between the balloons this increases the ability to exert adequate deployment force on stent portions 22 and 24. Similarly, post delivery dilatation may be used in order to further dilate the lesion from within the deployed stent 20.

Figure 7:
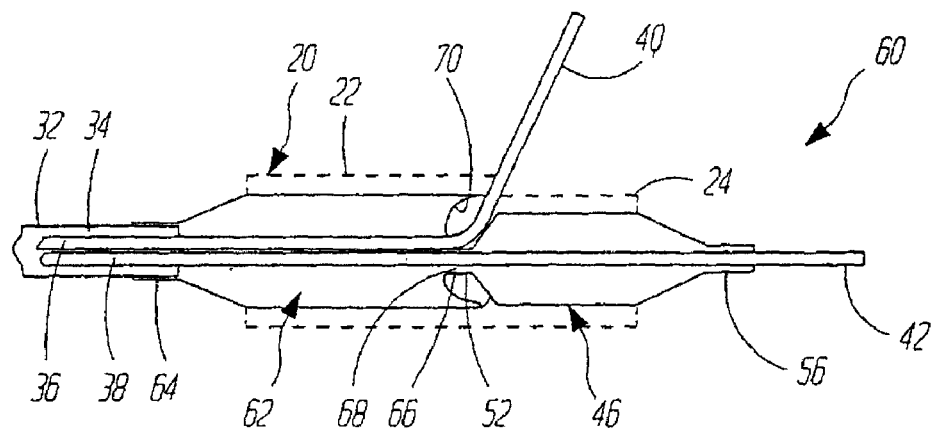
FIG. 7 illustrates another embodiment of a dual-balloon stent deployment system.

FIG. 7 illustrates a side view of another embodiment of a dual-balloon stent deployment system 60 in accordance with one aspect of the present invention. System 60 has a number of items which are similar to system 30 shown in FIG. 5, and those items are similarly numbered in FIG. 7. System 60 includes a proximal balloon 62 which has a proximal end 64 and a distal end 66. The proximal end 64 in balloon 62 is sealed about the distal end of catheter 32. The interior of balloon 62 communicates with lumen 34 of catheter 32. The distal end 66 of balloon 62 is formed in a cone configuration. A radially interior portion is sealed about guidewire tubes 36 and 38, leaving an inflation lumen 68 therebetween, which communicates with the interior of balloon 46. The radial outward portion of the distal end 66 of balloon 62, when inflated, assumes an outer diameter which is substantially the same as the maximum diameter of the remainder of balloon 62. However, the distal end 66 is formed in a reverse cone shape such that the radial outward portion of the distal end 66 is substantially tubular in shape. The balloon tapers proximally along a portion 70 to the inner diameter portion of balloon 62.

In this way, the outer diameter of balloon 62 obtains a substantially greater size, at its extreme distal end, than balloon 44 in system 30. This assists in deploying portion 22 of stent 20. Again, post-delivery dilatation may be used to further advance stent portions 22 and 24 toward the wall of vessels 12 and 14, respectively. Stent deployment system 60 is deployed in a similar fashion as stent deployment system 30, illustrated with respect to FIGS. 6A and 6B.

Figure 8A:
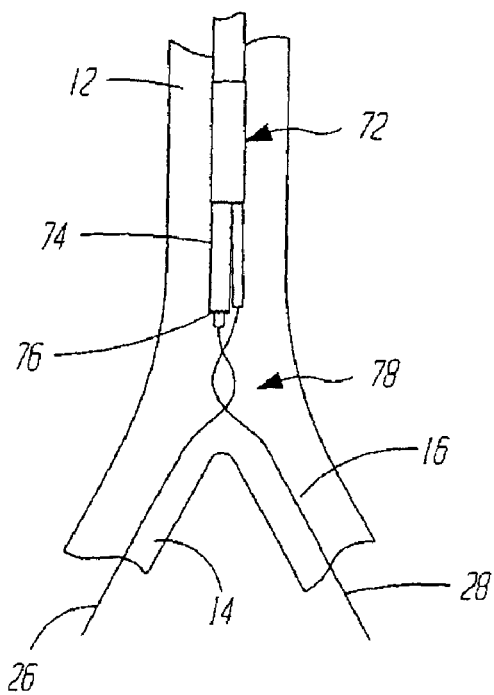
FIGS. 8A and 8B illustrate catching of a distal portion of a stent deployment system on crossed or tangled guidewires.
Figure 8B:
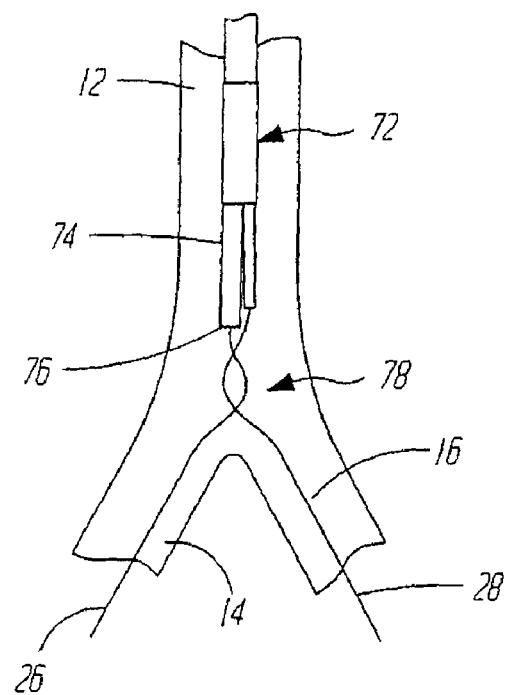

FIGS. 8A and 8B illustrate a problem which can be encountered in deploying a stent in a bifurcation. FIG. 8A illustrates a stent deployment system 72 located just proximally of bifurcation 10. Stent deployment system 72 includes a distal stent portion 74 which has a distal end 76. FIG. 8A also illustrates that guidewires 26 and 28 are crossed over one another in a cross-over region 78. As deployment system 72 is advanced distally, the distal end 76 of stent portion 74 encounters cross over region 78. FIG. 8B illustrates that the distal end 76 of stent portion 74 can actually catch, and hang up on, a portion of guidewire 28 which is crossed over guidewire 26. This makes it very difficult, if not impossible, to continue to advance stent deployment system 72 distally over guidewires 26 and 28. Instead, system 72 must be withdrawn proximally, and the guidewires 26 and 28 must be remanipulated or deployment system 72 must be torqued (rotated about its longitudinal axis) or otherwise maneuvered, in an attempt to loosen guidewire 28 from the distal end 76 of stent portion 74.

Figure 9A:
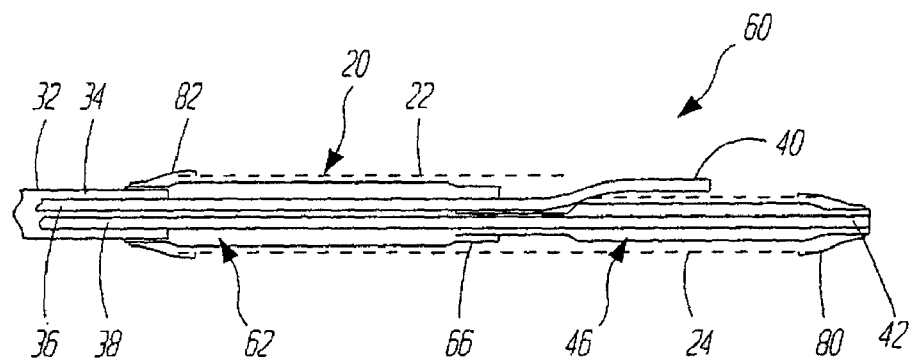
FIGS. 9A-9C illustrate a stent deployment system with a distal sleeve disposed thereabout.

FIG. 9A illustrates stent deployment system 60, as discussed with respect to FIG. 7, but with the addition of a distal sleeve 80 or a proximal sleeve 82 or both disposed about the distal end of stent portion 24 and the proximal end of stent portion 22, respectively. Distal sleeve 80 and proximal sleeve 82 are provided in order to minimize the likelihood that the longitudinal ends of stent 20 will catch or engage any unwanted obstacles, such as tissue or guidewires. The sieves 80 and 82 are described in greater detail in U.S. Pat. No. 4,950,227, which is fully incorporated herein by reference. Briefly, sleeves 80 and 82 are illustratively formed of silicone and are approximately 2 cm in length. Sleeve 80 is fixed to the distal end 42 of guidewire lumen 38 using adhesive or welding. Similarly, the proximal end of sleeve 82 is fixed to the distal end of catheter 32, using a suitable adhesive. Such adhesive may, for example, be comprised of a urethane bead. Sleeves 80 and 82 overlap stent portions 24 and 22, respectively, by a distance which is approximately 3 mm. Further, in one embodiment, sleeves 80 and 82 have tapered distal edges. In a further embodiment, sleeves 80 and 82 have tapered distal and proximal edges. This facilitates the transfer of system 60 within the vasculature, while decreasing the tendency to catch or engage undesired obstacles.

Figure 9B:
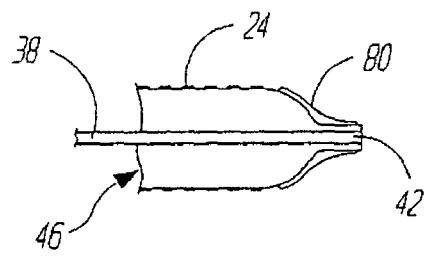
Figure 9C:
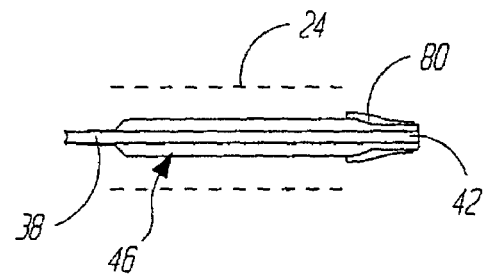

FIGS. 9B and 9C illustrate the deployment of stent portion 24 and the interaction of stent portion 24 with sleeve 80. A similar interaction is obtained between sleeve 82 and the proximal end of stent portion 22. As stent portion 24 is deployed, balloon 46 is inflated and the distal end of stent portion 24 is released from within sleeve 80. This is illustrated in FIG. 9B. Then, after stent portion 24 is deployed and balloon 46 is deflated (and thus radially retracted) sleeve 80 contracts about the distal end of balloon 46. The deflation of balloon 46 facilitates removal of balloon 46, as well as sleeve 80, from within the deployed stent portion 24, as deployment system 60 is axially removed from the vasculature. It should be noted that sleeves 80 and 82 can be used on substantially any of the embodiments described herein.

Figure 10:
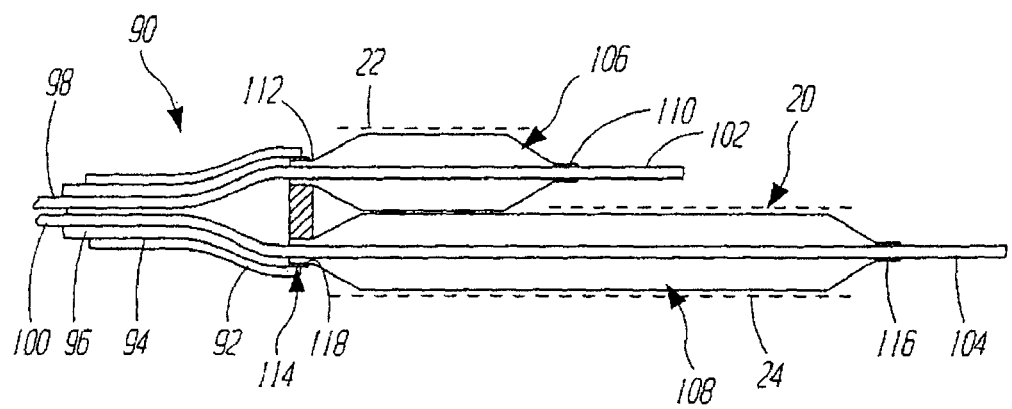
FIG. 10 illustrates another embodiment of a dual-balloon stent deployment system.

FIG. 10 illustrates another dual-balloon stent deployment system 90 in accordance with one aspect of the present invention. System 90 includes an outer sheath 92, an inner sheath 94 defining an inflation lumen 96, a plurality of guidewire lumens 98 and 100, each having distal ends 102 and 104, respectively. System 90 also includes first balloon 106 and second balloon 108. First balloon 106 has a distal end 110 which is sealed about the outer surface of guidewire lumen 102. Balloon 106 also has a proximal end 112 which is sealed within a disc 114 which is sealed (such as through adhesive) to the inside of the distal end of catheter 94. Balloon 108 has a distal end 116 which is sealed about the outer surface of guidewire lumen 104, and a proximal end 118 which is sealed within disc 114. The interior of balloons 106 and 108 are in fluid communication with the lumen 96 formed by inner catheter 94. This provides an arrangement to provide fluid under pressure to inflate balloons 106 and 108. It should be noted that, instead of using disc 114, the inside of the distal end of catheter 94 can simply be filled with adhesive using a technique commonly referred to as potting.

Balloons 106 and 108 can either have the same, or different, deployed diameters. However, balloon 108 may have a greater longitudinal length than balloon 106. Therefore, stent portion 22 of stent 20 can be deployed by inflating both balloons 106 and 108 to drive stent portion 22 into its higher profile, deployed position. By contrast, stent portion 24 is disposed only about the distal part of balloon 108, distal of balloon 106. Thus, stent portion 24 is deployed by the inflation of balloon 108. System 90 is used to deploy stent 20 in a similar fashion to that described with respect to system 30 in FIGS. 6A and 6B.

Figure 10A:
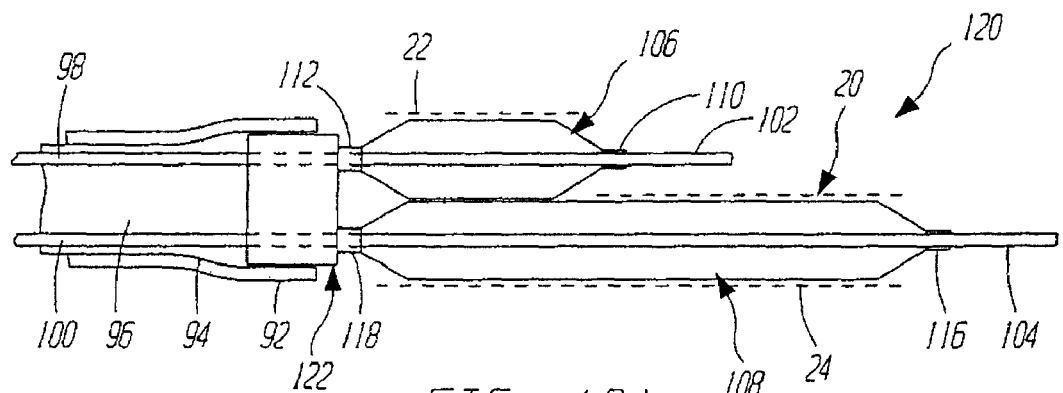
FIGS. 10A-10C illustrate another embodiment of a dual-balloon stent deployment system.
Figure 10B:
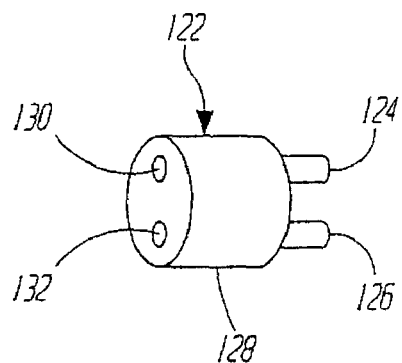
Figure 10C:
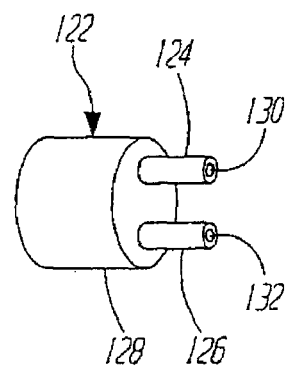

FIGS. 10A-10C illustrate another stent deployment system 120. System 120 is similar to system 90 illustrated in FIG. 10, and similar items are similarly numbered. However, rather than having a disc 114 disposed at the distal end of catheter 94, system 120 has a plug member 122 (which is also illustrated in FIGS. 10B and 10C). Plug member 122 has an exterior surface which snugly fits within the interior of the distal end of catheter 94, and is secured therein, such as by frictional fit or suitable adhesive. Plug member 122 also has generally tubular extensions 124 and 126 which extend from a body 128 thereof. A pair of lumens 130 and 132 extend through body 128 and through extension members 124 and 126, respectively. Lumens 130 and 132 are larger than guidewire lumens 98 and 100 such that guidewire lumens 98 and 100 can pass therethrough, and still leave an area which provides fluid communication between lumen 96 of catheter 94 and the interior of balloons 106 and 108, respectively. This provides a mechanism by which balloons 106 and 108 can be inflated through the infusion of pressurized fluid through lumen 96 in catheter 94.

In addition, the proximal ends 112 and 118 of balloons 106 and 108 are illustratively fastened about the exterior of extension members 124 and 126, respectively. Such fastening can take any suitable form, such as through adhesive.

Figure 11A:
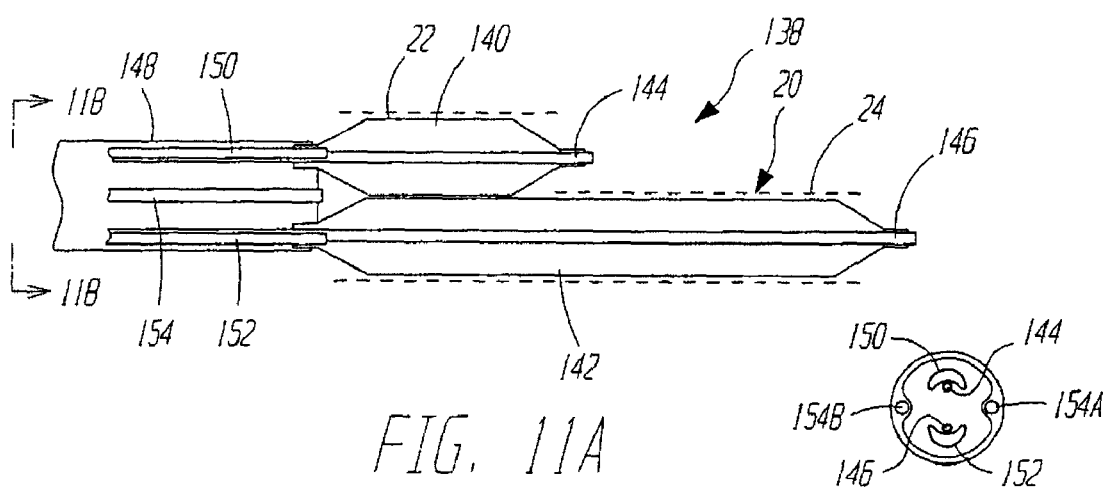
FIGS. 11A and 11B illustrate another embodiment of a dual-balloon stent deployment system.
Figure 11B:
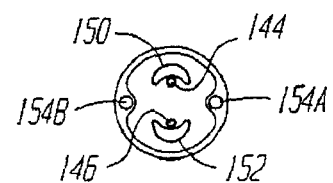

FIGS. 11A and 11B illustrate yet another embodiment of a stent deployment system 138 in accordance with another aspect of the present invention. System 138 includes a first balloon 140 and a second balloon 142. Each balloon is disposed about a guidewire lumen 144 and 146, respectively. A proximal catheter 148 is provided with two separate inflation lumens 150 and 152. Inflation lumen 150 is provided to inflate balloon 140 while inflation lumen 152 is provided to inflate balloon 142. The proximal end of balloons 140 and 142 are sealably connected about inflation lumens 150 and 152 and guidewire lumens 144 and 146.

Similarly, catheter 148 is also provided with a stiffening member 154. Stiffening member 154 is preferably a stiffening wire (or a pair of stiffening wires or a hypotube) which runs at least through a distal portion of catheter 148, and is fastened thereto, to provide increased pushability, and increased torquability.

FIG. 11B is a cross-sectional view of catheter 148 taken along section lines 11B-11B shown in FIG. 11A. FIG. 11B shows that, in one illustrative embodiment, catheter 148 includes a pair of stiffening members 154A and 154B which are either embedded within, or fixedly secured to, the wall of catheter 148. Similarly, FIG. 11B better illustrates that inflation lumens 150 and 152 are generally kidney-shaped (or shaped in a generally hemispherical shape) and extend partially about the guidewire lumens 144 and 146, respectively System 138 is used to deploy stent 20 in a fashion similar to system 30 illustrated in FIGS. 6A and 6B.

Figure 12A:
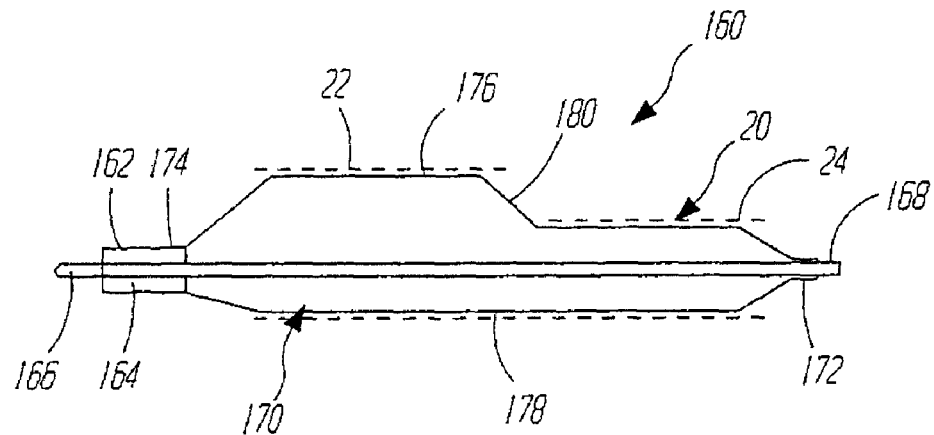
FIGS. 12A-12C illustrate a stepped-balloon stent deployment system.

FIG. 12A is a side view of another embodiment of a stent deployment system 160 in accordance with one aspect of the present invention. System 160 includes a catheter 162 with a lumen 164 therein. A guidewire lumen 166 extends through lumen 164 to a distal end 168 of the guidewire lumen. System 160 also includes a stepped balloon 170. Stepped balloon 170 has a distal end 172 sealably connected about the outer surface of guidewire lumen 168. Balloon 170 also has a proximal end 174 sealably connected about the external surface of catheter 162. In addition, balloon 170 has a first portion 176 which has a first inflated outer diameter and a second portion 178 which has a second inflated outer diameter, less than the first inflated outer diameter of portion 176. Balloon 170 has a step region 180 which defines the transition between portion 176 and 178. The step region 180, in the embodiment illustrated in FIG. 12A, is simply a steeply tapering portion which extends from the inflated outer diameter of balloon portion 178 to the inflated outer diameter of balloon portion 176. Balloon 170 is preferably formed of a conventional balloon material preformed into the stepped shape illustrated generally in FIG. 12A.

Thus, stent 20 can be deployed using only a single balloon 170. The smaller diameter stent portion 24 is disposed over balloon portion 178, while the larger diameter balloon stent portion 22 is disposed over balloon portion 176.

Figure 12B:
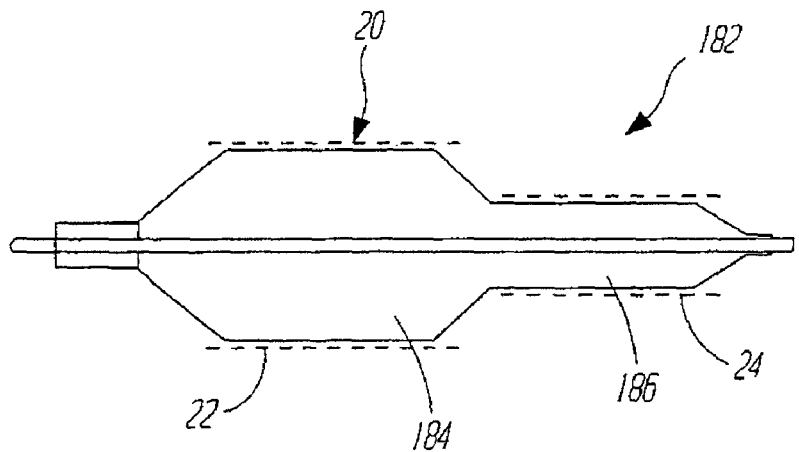
Figure 12C:
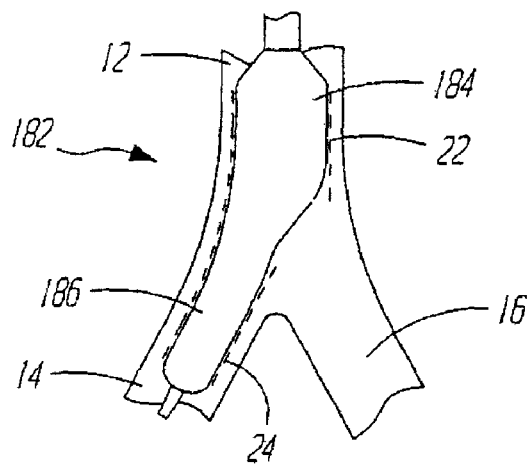

FIG. 12B illustrates another stepped balloon 182. Balloon 182 also includes first and second portions 184 and 186. However, the step in balloon 182 is generally concentric, rather than eccentric as described with respect to FIG. 12A. FIG. 12C illustrates balloon 182 disposed within bifurcation 10. In one illustrative embodiment, stent 20 has section 22, which is weaker than section 24. Due to the strength of stent 20, the step in balloon 182 moves or shifts from being concentric, to being non-concentric, as illustrated in FIG. 12C. The eccentricity shifts towards the open cell (or weaker section) of stent 22.

Figure 13A:
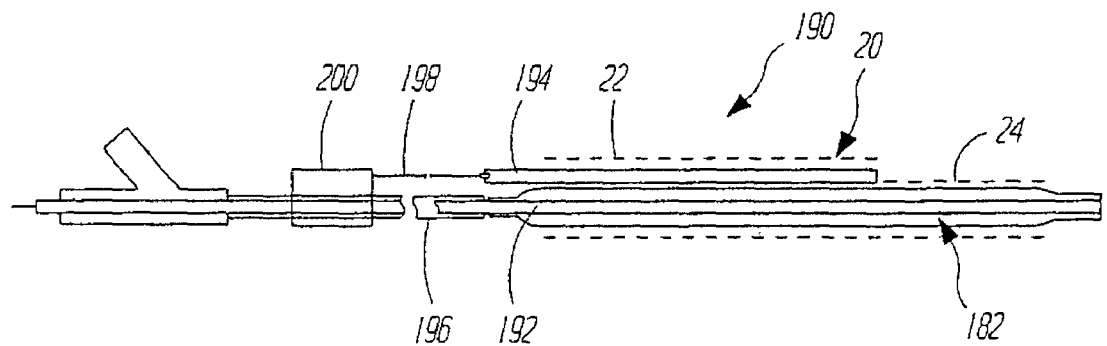
FIGS. 13A-13C illustrate a retractable stent deployment system.
Figure 13B:
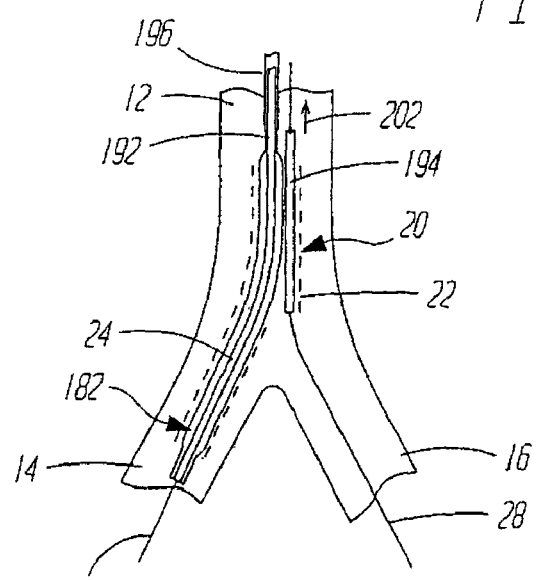
Figure 13C:
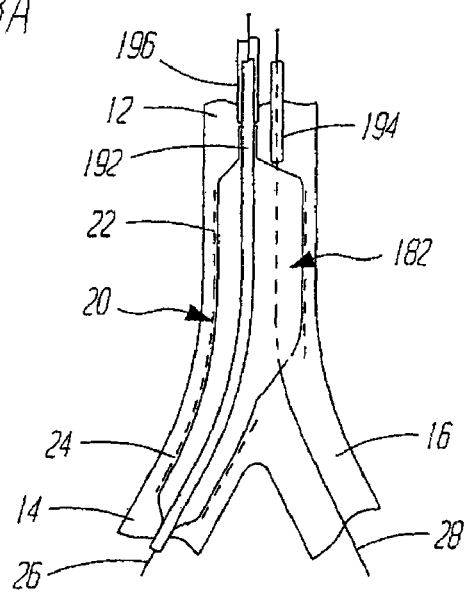

FIGS. 13A-13C illustrate another stent deployment system 190 in accordance with one aspect of the present invention. Deployment system 190 includes stepped balloon 182 with a guidewire lumen 192 extending therethrough. Stent 20 is disposed about balloon 182. In addition, within stent portion 22, and on the exterior of balloon 182, is provided a second guidewire lumen 194. A proximal catheter 196 is coupled to fluidly communicate with the interior of balloon 182. A pull wire 198 is coupled to the proximal end of guidewire lumen 194 and to a pull sleeve 200 slidably disposed about catheter 196, generally at the proximal end of catheter 196.

FIGS. 13A and 13B illustrate the insertion of system 190 for deployment of stent 20. FIG. 13B illustrates that system 190 is advanced through the vasculature over guidewires 26 and 28 such that the distal end of balloon 182 (and stent portion 24) resides within branch vessel 14. Stent 20 is deployed under relatively low pressure to pre-dilate the stent. Next, guidewire lumen 194 is withdrawn proximally in the direction indicated by arrow 202, by user withdrawal of sleeve 20 proximally over catheter 196.

Balloon 182 is then further inflated to a relatively high pressure to post-dilate the stent, as illustrated in FIG. 13C. This acts to deploy stent 20 outwardly causing the outer surface of stent 20 to frictionally engage the interior surface of parent vessel 12 in branch vessel 14. Balloon 182 is then deflated and the system is withdrawn from the vasculature, leaving stent 20 in place in bifurcation 10.

Figure 14A:
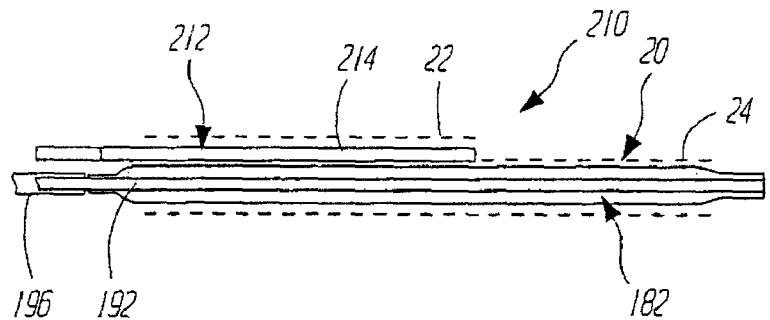

FIGS. 14A-14C illustrate another stent deployment system 210 in accordance with one aspect of the present invention. System 210 is similar to system 190 described with respect to FIGS. 13A-13C, and similar items are similarly numbered. However, system 210 allows guidewire lumen 194 to remain in place, adjacent balloon 182, during deployment of stent 20. Therefore, rather than having a removable guidewire lumen 194, system 210 includes guidewire lumen 212. As in system 190, guidewire lumen 212 resides within portion 22 of stent 20, but on the exterior of balloon 182.

FIG. 14B illustrates that system 210 is inserted within bifurcation 10 in a manner similar to system 190 (illustrated in FIG. 13B) However, guidewire lumen 212 remains in place during inflation of balloon 182, as shown in FIG. 14C. In one preferred embodiment, at least the distal portion 214 of guidewire lumen 212 is collapsible. Therefore, as balloon 182 is inflated, the distal portion 214 (which resides within stent 20) of guidewire lumen 212 collapses against the inner wall of stent portion 22, about guidewire 28. The exterior periphery of balloon 182 drives deployment of stent portion 22, by exerting pressure on the collapsible portion 214 of guidewire lumen 212.

In another embodiment, the distal portion 214 of guidewire tube 212 is substantially rigid. When balloon 182 is inflated, tube 212 stays in place. Therefore, inflation of balloon 182 exerts pressure on tube 212 causing stent portion 22 to deploy radially outwardly.

FIGS. 15A-15C illustrate another embodiment of the present invention. For purposes of the present discussion, system 210 illustrated with respect to FIGS. 14A-14C is illustrated in FIG. 15A, along with a torquing system 220. However, it will be appreciated that torquing system 220 can be used with substantially any of the other embodiments discussed herein.

Torquing system 220 includes a shaft 222 disposed about guidewire lumen 212 and catheter 196. System 220 also includes a slidable sleeve 224 which is slidably engageable with the exterior surface of shaft 222. Sleeve 224 is preferably substantially rigid when compared with, for example, catheter 196. When sleeve 224 slidably engages the surface of shaft 222, the user can torque or rotate sleeve 222 and thus substantially increase the torquability (or rotatability) of stent deployment system 210.

FIG. 15B is a rear perspective view of one embodiment of shaft 222 and sleeve 224. In one embodiment, shaft 222 is a relatively flexible and resilient shaft, made of suitable polymer material which is commercially available and conventionally used to make percutaneous catheters. However, shaft 222 includes flattened wall surfaces 226 disposed on generally opposite sides thereof. Sleeve 224 is either a full hypotube, or a portion thereof, which also has flattened sides 228 which are spaced from one another just far enough to slidably receive the flattened surfaces 226 of shaft 222. Therefore, when the user advances sleeve 224 distally such that the sides 228 engage surfaces 226, the user can more easily torque system 210.

FIG. 15C illustrates an alternative embodiment of shaft 222 and sleeve 224. In the embodiment illustrated in FIG. 15C, shaft 222 has one or more slots 230 defined about the perimeter thereof. Similarly, sleeve 224 has corresponding radially inwardly directed protrusions 232 disposed thereabout. Protrusions 232 are sized just smaller than slots 230. Therefore, as the user slides sleeve 224 distally, protrusions 232 slidably engage, and slide within, slots 230. Since sleeve 224 is made of a relatively rigid material, it can be used to torque, or steer, system 210 within the vasculature.

Thus, it can be seen that the present invention provides a system for deploying a stent at a bifurcation. The system includes a variety of dual-balloon delivery and deployment systems. In another embodiment, the system includes a stepped balloon arrangement. Further, in another embodiment, the system includes a mechanism by which torquability can be increased to make positioning of the stent delivery system within the vasculature much easier.

Although the present invention has been described with reference to preferred embodiments, workers skilled in the art will recognize that changes may be made in form and detail without departing from the spirit and scope of the invention.

The invention claimed is:

1. A dual balloon catheter comprising:
   an elongate catheter body having a distal end, first and second guide wire tubes extending therethrough and an inflation lumen therein;
   a first proximal balloon having a proximal portion bonded to the distal end of the catheter, and a distal portion bonded partially to the first guide wire tube;
   a second distal balloon having a proximal portion bonded partially to the distal portion of the first proximal balloon and bonded partially to the first guide wire tube, and a distal portion bonded to the second guide wire tube distally of the first balloon, the proximal and distal balloons in fluid communication with the inflation lumen; and
   a guide wire port positioned longitudinally between the first and second balloons and in communication with the first guide wire tube.

2. The dual balloon catheter of claim 1 wherein the distal portion of the first balloon is bonded partially to the proximal portion of the second balloon.

3. The dual balloon catheter of claim 1 wherein the second guide wire tube has a distal exit port distal of the distal portion of the second balloon.

4. The dual balloon catheter of claim 1 wherein a distal waist of the first balloon to closely fits about a portion of a proximal waist of the second balloon.

5. The dual balloon catheter of claim 1 wherein the first balloon has a first axis offset from a second axis of the second balloon.

6. A bifurcated stent delivery device comprising:
   a catheter having first and second guide wire tubes extending therethrough and an at least one inflation lumen therein;
   an expansion member comprising a proximal balloon having a proximal end bonded to a distal end of the catheter, and a distal balloon having a distal end bonded to the second guide wire tube, wherein a distal end of the proximal balloon is bonded partially to the first guide wire tube and partially to a proximal end of the distal balloon, wherein the proximal and distal balloons are in fluid communication with the at least one inflation lumen, wherein the proximal balloon has a first expanded diameter and the distal balloon has a second expanded diameter, wherein the first expanded diameter is greater than the second expanded diameter; and
   a stent sleeve fixed to the catheter such that the stent sleeve surrounds at least one of the distal end of the distal balloon or the proximal end of the proximal balloon, the stent sleeve configured to protect or secure an end of a stent.

7. The bifurcated stent delivery device of claim 6 further comprising a guide wire port in communication with the first guide wire tube and located between the distal balloon and the proximal balloon.

8. The catheter of claim 6 further comprising a second inflation lumen therethrough.

9. A bifurcated stent delivery device comprising:
   a catheter including a first guidewire tube, a second guidewire tube, and at least one inflation lumen;
   a balloon assembly including a proximal portion and a distal portion, the proximal portion being in fluid communication with the at least one inflation lumen and having a first expanded diameter when inflated, the distal portion being in fluid communication with the at least one inflation lumen and having a second expanded diameter when inflated, the first expanded diameter being greater than the second expanded diameter; and a guidewire port located at a transition area between the distal portion of the balloon assembly and the proximal portion of the balloon assembly, wherein a distal end of the proximal portion of the balloon assembly is sealed partially to the first guidewire tube and sealed partially to a proximal end of the distal portion of the balloon assembly at the transition area, and the first guidewire tube extends through the guidewire port.

10. The bifurcated stent delivery device of claim 9 wherein the proximal portion of the balloon assembly includes a first proximal balloon having a proximal end bonded to a distal end of the catheter, and the distal portion of the balloon assembly includes a second balloon having a distal end bonded to the second guidewire tube.

11. The bifurcated stent delivery device of claim 9 wherein the second guidewire tube has a distal portion distal of a distal end of the distal portion of the balloon assembly.

12. The bifurcated stent delivery device of claim 9 wherein the catheter includes a second inflation lumen.

13. The bifurcated stent delivery device of claim 9 wherein the proximal portion of the balloon assembly has a central axis and the distal portion of the balloon assembly has a central axis, the axis of the proximal portion being co-linear with the axis of the distal portion.

14. The bifurcated stent delivery device of claim 9 wherein the proximal portion has a proximal waist, a distal waist, and a body therebetween and the distal portion has a proximal waist, a distal waist, and a body therebetween.

15. The bifurcated stent delivery device of claim 14 wherein the guidewire port is positioned between the distal waist of the proximal portion and the proximal waist of the distal portion.

16. The bifurcated stent delivery device of claim 14 wherein the distal waist of the proximal portion is bonded partially to a proximal end of the proximal waist of the distal portion providing a sealed fluid path connecting the proximal portion to the distal portion.

17. The bifurcated stent delivery device of claim 14 wherein the distal waist of the proximal portion forms a reverse cone that is sized and configured to closely wrap over the proximal waist of the distal portion.

\* \* \* \* \*